(12) United States Patent
Dirauf et al.

(10) Patent No.: US 10,932,731 B2
(45) Date of Patent: Mar. 2, 2021

(54) METHOD FOR OPERATING AN AT LEAST PARTIALLY AUTONOMOUSLY MOVING, MOBILE MEDICAL UNIT, AND MOBILE MEDICAL UNIT

(71) Applicant: Siemens Healthcare GmbH, Erlangen (DE)

(72) Inventors: Franz Dirauf, Ebensfeld (DE); Verena Schmidt, Erbendorf (DE)

(73) Assignee: SIEMENS HEALTHCARE GMBH, Erlangen (DE)

(*) Notice: Subject to any disclaimer, the term of this patent is extended or adjusted under 35 U.S.C. 154(b) by 98 days.

(21) Appl. No.: 16/311,746

(22) PCT Filed: Jun. 2, 2017

(86) PCT No.: PCT/EP2017/063419
§ 371 (c)(1),
(2) Date: Dec. 20, 2018

(87) PCT Pub. No.: WO2018/007076
PCT Pub. Date: Jan. 11, 2018

(65) Prior Publication Data
US 2019/0209104 A1    Jul. 11, 2019

(30) Foreign Application Priority Data
Jul. 4, 2016   (DE) .......................... 10 2016 212 077

(51) Int. Cl.
*A61B 6/10* (2006.01)
*G05D 1/02* (2020.01)
(Continued)

(52) U.S. Cl.
CPC ............ *A61B 6/102* (2013.01); *A61B 6/4405* (2013.01); *G05D 1/0088* (2013.01);
(Continued)

(58) Field of Classification Search
USPC .......................................................... 701/28
See application file for complete search history.

(56) References Cited

U.S. PATENT DOCUMENTS

2004/0015266 A1* 1/2004 Skoog ................. G05D 1/0891
700/245
2004/0093650 A1* 5/2004 Martins .................... B25J 5/007
180/167
(Continued)

FOREIGN PATENT DOCUMENTS

DE     10352952 A1    6/2005
DE     102008046346 A1    3/2010
(Continued)

OTHER PUBLICATIONS

Notification of Transmittal of the International Search Report and Written Opinion (PCT/ISA/220) for PCT International Application No. PCT/EP2017/063419 dated Aug. 23, 2017.
(Continued)

*Primary Examiner* — Tyler D Paige
(74) *Attorney, Agent, or Firm* — Harness, Dickey & Pierce, P.L.C.

(57) ABSTRACT

A method is for operating an at least partially autonomously moving, mobile medical unit, which has at least one sensing device for detecting possible collision objects in the environment of the unit and a control device, which evaluates the sensing data of the sensing device and which is designed to at least partially autonomously operate the movement of the unit while performing a collision protection function. In an embodiment of the method, a possible collision object described by the sensing data is classified by evaluating the sensing data and the classification is taken into consideration in the autonomous operation of the unit, in particular in the calculation of a trajectory to be traveled.

28 Claims, 2 Drawing Sheets

(51) Int. Cl.
*G05D 1/00* (2006.01)
*A61B 6/00* (2006.01)

(52) U.S. Cl.
CPC ......... *G05D 1/0212* (2013.01); *G05D 1/0214* (2013.01); *G05D 1/0246* (2013.01); *G05D 1/0255* (2013.01); *G05D 2201/0206* (2013.01)

(56) References Cited

U.S. PATENT DOCUMENTS

| | | | |
|---|---|---|---|
| 2005/0154265 A1* | 7/2005 | Miro | G10L 15/26 600/300 |
| 2007/0192910 A1* | 8/2007 | Vu | G05D 1/0274 700/245 |
| 2009/0043440 A1* | 2/2009 | Matsukawa | G05D 1/0214 701/25 |
| 2011/0288684 A1* | 11/2011 | Farlow | G05D 1/0038 700/264 |
| 2012/0029697 A1 | 2/2012 | Ota et al. | |
| 2012/0182392 A1 | 7/2012 | Kearns et al. | |
| 2014/0148989 A1 | 5/2014 | Ueda et al. | |
| 2015/0007390 A1 | 1/2015 | Haider et al. | |

FOREIGN PATENT DOCUMENTS

| | | |
|---|---|---|
| DE | 102008046348 A1 | 3/2010 |
| DE | 102010003429 A1 | 10/2011 |
| DE | 112011105449 T5 | 4/2014 |
| DE | 102013213213 A1 | 1/2015 |
| DE | 102015212886 A1 | 5/2016 |
| WO | WO 2011146259 A2 | 11/2011 |

OTHER PUBLICATIONS

International Search Report (PCT/ISA/210) for PCT International Application No. PCT/EP2017/063419 dated Aug. 23, 2017.
Written Opinion (PCT/ISA/237) for PCT International Application No. PCT/EP2017/063419 dated Aug. 23, 2017.
German Office Action for DE 102016212077.8 dated Feb. 9, 2017.
German Office Action dated Jul. 22, 2019.
European Office Action for European Patent Application No. 17729070.7 dated Jun. 8, 2020.
Korean Office Action for Korean Patent Application No. 10-2019-7000220 dated Jun. 15, 2020 and English translation thereof.
Korean Notice of Allowance dated Dec. 30, 2020.

* cited by examiner

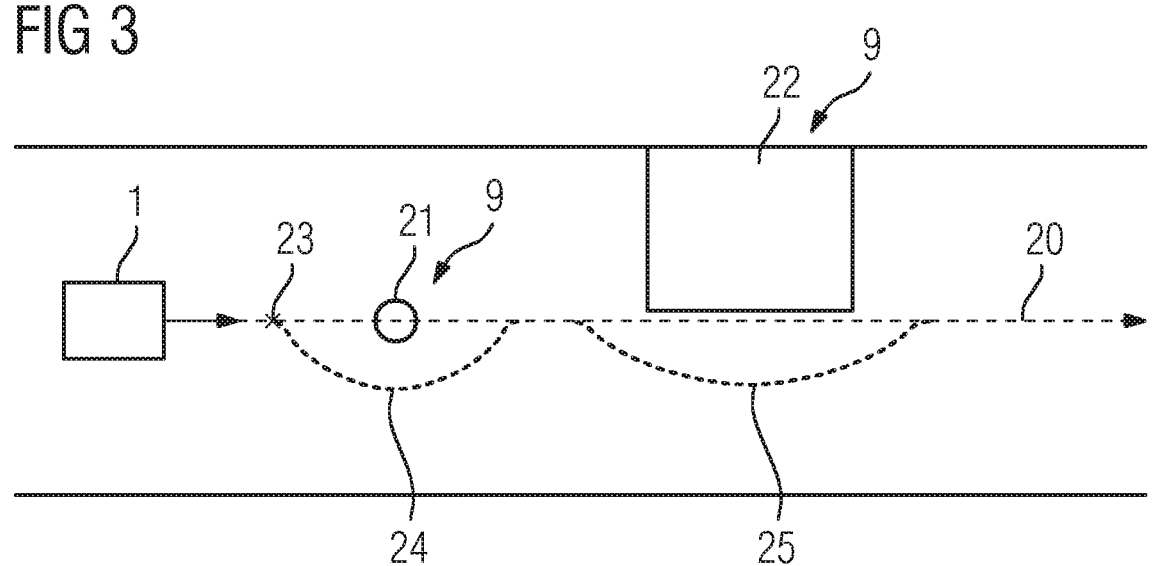
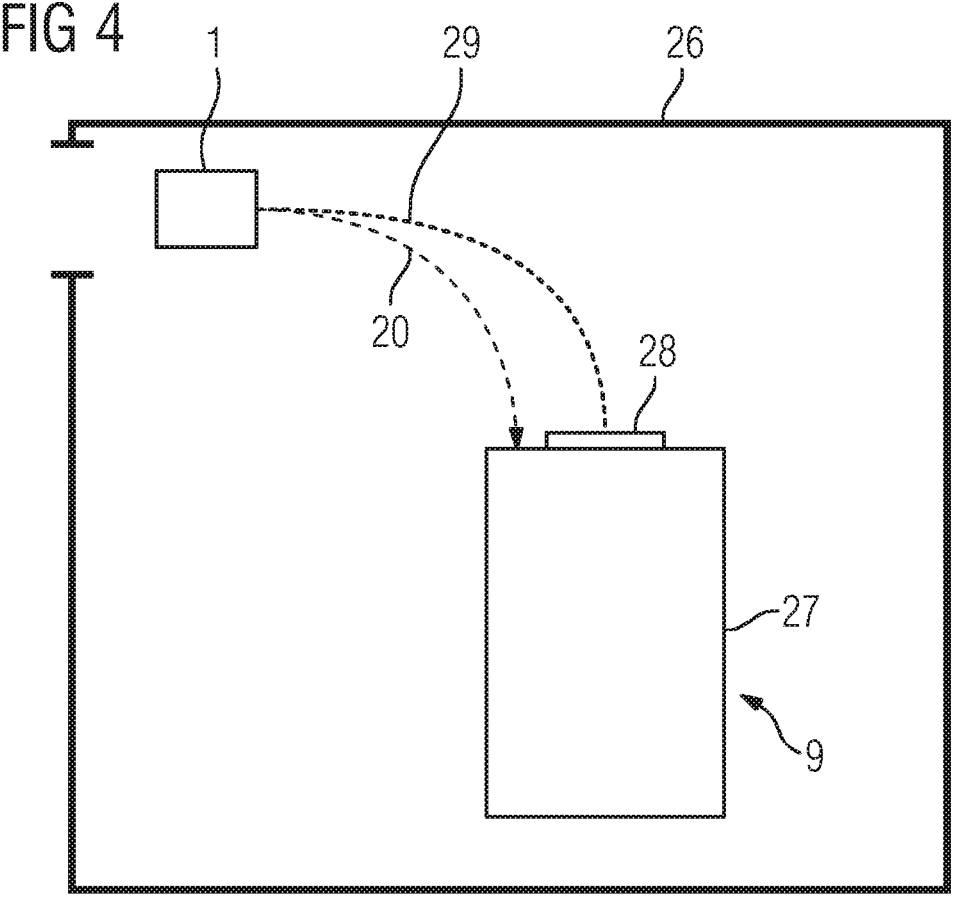

US 10,932,731 B2

METHOD FOR OPERATING AN AT LEAST PARTIALLY AUTONOMOUSLY MOVING, MOBILE MEDICAL UNIT, AND MOBILE MEDICAL UNIT

PRIORITY STATEMENT

This application is the national phase under 35 U.S.C. § 371 of PCT International Application No. PCT/EP2017/063419 which has an International filing date of Jun. 2, 2017, which designated the United States of America and which claims priority to German Patent Application No. DE 102016212077.8 filed Jul. 4, 2016, the entire contents of which are hereby incorporated herein by reference.

FIELD

An embodiment of the invention generally relates to a method for operating an at least partially autonomously moving, mobile medical unit, which has at least one sensing device for detecting possible collision objects in the environment of the unit and a control device, which evaluates the sensing data of the sensing device and which is designed to at least partially autonomously operate the movement of the unit while performing a collision protection function. An embodiment of the invention also relates to a mobile medical unit.

In the medical sector, units have already been proposed which, for example, are intended to move automatically, in other words, autonomously, in a hospital and/or in a radiology department, for example, to a destination. In the medical sector, it is essential to protect people, in particular, patients, their visitors and medical personnel, as well as other, if applicable, valuable medical equipment and devices.

Therefore, such autonomously moving medical units usually have a collision protection function provided, wherein usually a sensor system of the medical unit or an external sensor system is used to detect objects in the path of movement of the mobile medical unit and to avoid a collision by way of a corresponding adaptation of the autonomous operation of the mobile medical unit. In particular, collision protection functions which are realized by control devices of mobile medical units are usually designed such that when a possible collision object enters a potentially graduated warning zone, the units are moved more slowly or stopped.

SUMMARY

However, the inventors have discovered that it is problematic that in some situations in which the mobile medical unit is intended to interact with other objects, a collision with this object may be desired. For example, if an autonomously movable C-arm approaches patient positioning equipment as a mobile medical unit, the patient positioning equipment will be in the collision area or graduated warning zone. Another example is the docking procedure of patient positioning equipment as a mobile medical unit to a magnetic resonance facility or other imaging device. Here, for example, the autonomous operation of the movement must be ended and the interaction manually initiated. A further disadvantage of known collision protection functions is that the reactions of the mobile medical unit to a possible collision object in the future path of movement must be designed for the possible collision object requiring the maximum safety, which could potentially result in the autonomous movement of the mobile medical unit being completely canceled.

At least one embodiment of the invention therefore specifies an improved method for operating a mobile medical unit which, in particular, permits interaction with other objects and/or establishes a larger area of use for autonomous movement.

In at least one embodiment, a method is provided wherein a possible collision object, described by the sensing data, is classified by evaluating the sensing data and the classification is taken into consideration in the autonomous operation of the unit, in particular, in the calculation of a trajectory to be traveled.

Possible collision objects may be all the objects in the (detected) environment of the mobile medical unit, wherein the notion of the possible collision object may also be restricted to those which actually conflict with a currently planned and/or predicted, trajectory to be traveled. For example, for selection as a relevant surrounding object, that is to say, as a possible collision object which is to be classified, a collision value describing a probability of collision and/or a predicted collision taking place can be compared with a threshold value or otherwise taken into consideration.

At least one embodiment of the invention therefore proposes the provision of a mobile medical unit with the option of identifying and/or classifying a potential collision object. In this manner, the possibility arises of implementing special rules of conduct with regard to certain object classes and thus enabling more flexible, significantly improved autonomous operation of the movement of the mobile medical unit since specific properties of objects of an object class can be addressed and/or interaction with objects of a specific object class can be selectively permitted.

At least one embodiment of the invention therefore is directed to a method for operating an at least partially autonomously moving, mobile medical unit including at least one sensing device to detect possible collision objects in an environment of the unit and including a control device, to evaluate sensing data of the sensing device and designed to at least partially autonomously operate movement of the mobile medical unit while performing a collision protection function, the method comprising:

classifying a possible collision object, described by the sensing data, by evaluating the sensing data and taking, into consideration in the autonomous operation of the unit, the possible collision object classified by the classifying;

adapting the control device to at least one operating parameter relating to a behavior towards the possible collision object classified, in a context of at least partially autonomous movement operation of the mobile medical unit for possible collision partners of at least one selected object class.

At least one embodiment of the invention therefore is directed to a mobile medical unit, comprising:

at least one sensing device to detect possible collision objects in an environment of the mobile medical unit; and a control device to evaluate sensing data of the at least one sensing device and designed to at least partially autonomously operate movement of the mobile medical unit while performing a collision protection function, the control device being further configured to classify a possible collision object, described by the sensing data, by evaluating the sensing data and taking, into consideration in the autonomous operation of the unit, the possible collision object classified by the classifying; and adapt to at least one operating parameter relating to a behavior towards the possible collision object classified, in a context of at least partially autonomous movement operation of the mobile medical unit for possible collision partners of at least one selected object class.

In at least one embodiment, a method is provided wherein a possible collision object, described by the sensing data, is classified by evaluating the sensing data and the classification is taken into consideration in the autonomous operation of the unit, in particular, in the calculation of a trajectory to be traveled.

In addition to the method, at least one embodiment of the invention also relates to a mobile medical unit, which has at least one sensing device for detecting possible collision objects in the environment of the unit and a control device which evaluates the sensing data of the sensing device and which is designed to at least partially autonomously operate the movement of the unit while performing the collision protection function which is characterized in that the control device is designed to perform the method according to at least one embodiment of the invention.

BRIEF DESCRIPTION OF THE DRAWINGS

Further advantages and details of the present invention will emerge from the example embodiments described hereinafter and with reference to the diagram. The diagram shows.

DETAILED DESCRIPTION OF THE EXAMPLE EMBODIMENTS

Figure 1:
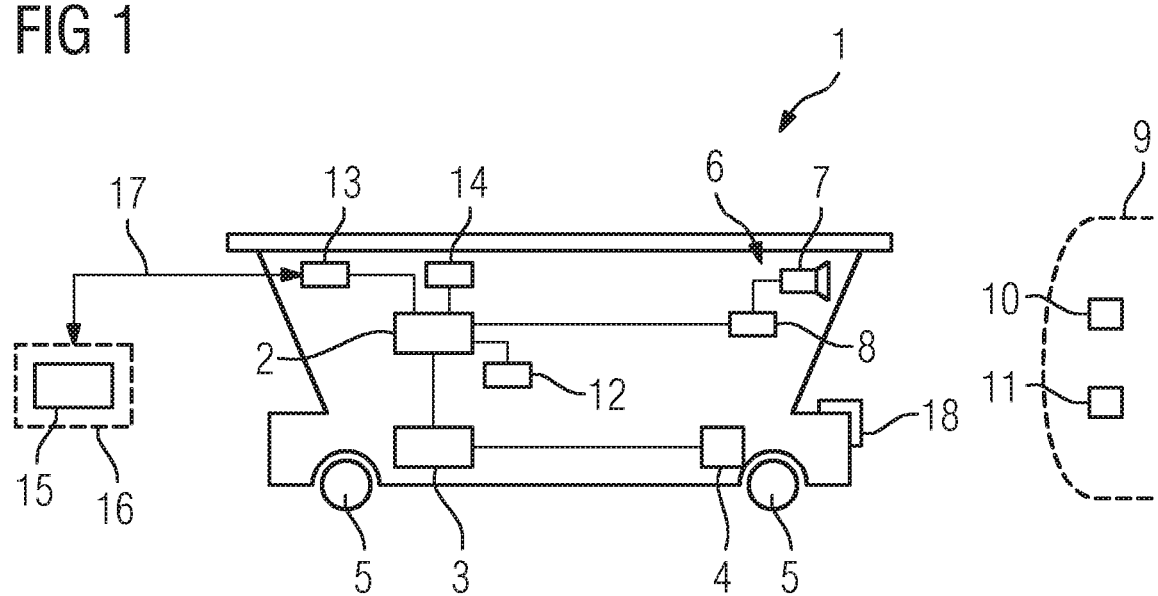
FIG. 1 A mobile medical unit according to an embodiment of the invention.

In at least one embodiment, a method is provided wherein a possible collision object, described by the sensing data, is classified by evaluating the sensing data and the classification is taken into consideration in the autonomous operation of the unit, in particular, in the calculation of a trajectory to be traveled.

Possible collision objects may be all the objects in the (detected) environment of the mobile medical unit, wherein the notion of the possible collision object may also be restricted to those which actually conflict with a currently planned and/or predicted, trajectory to be traveled. For example, for selection as a relevant surrounding object, that is to say, as a possible collision object which is to be classified, a collision value describing a probability of collision and/or a predicted collision taking place can be compared with a threshold value or otherwise taken into consideration.

At least one embodiment of the invention therefore proposes the provision of a mobile medical unit with the option of identifying and/or classifying a potential collision object. In this manner, the possibility arises of implementing special rules of conduct with regard to certain object classes and thus enabling more flexible, significantly improved autonomous operation of the movement of the mobile medical unit since specific properties of objects of an object class can be addressed and/or interaction with objects of a specific object class can be selectively permitted.

In simple applications, it already suffices if the classification of a possible collision object is identified as belonging to a certain object class or not belonging to this object class (in other words, belonging to an object class comprising all the other objects). For example, in the case of patient positioning equipment for docking, in particular, of a patient table, as a mobile medical unit the particular object class may comprise objects to which the patient positioning equipment is to dock, for example, magnetic resonance facilities. Interaction can then be permitted for this, for example, by suspending the collision protection function for this possible collision object in the simplest case. Thus, objects not belonging to the particular object class would be protected, for example, by way of circumvention, while interaction is not impaired. Generally, however, there will be many different object classes for which special rules of conduct can be defined.

In this manner, context-sensitive route planning and/or context-sensitive autonomous movement is produced particularly advantageously, which means that the reaction of the mobile medical unit to possible obstacles in the travel range depends on the classification of the possible collision object and, in particular, its properties.

The scope of application for the autonomous operation of mobile medical units is expanded by enabling interactions to be permitted and/or the object class with the greatest need for protection not necessarily having to be used as the basis.

It has already been noted at this point that reactions by the mobile medical unit to possible collision objects, if applicable also dependent on the object class, may comprise an adaptation of the speed, a calculation of a new trajectory to be traveled, and/or a waiting period. An interaction by way of the present method is also now conceivable.

The sensing device may preferably comprise at least one imaging sensor, in particular, a camera, wherein the control device evaluates the sensing data of the imaging sensor by way of image processing, and/or a sensing device comprising a readout device for a radio marker, in particular, an RFID chip, of the possible collision object is used. For example, a camera may therefore be used, the image data of which can be evaluated as sensing data, for example, by way of corresponding, generally known image processing algorithms, to enable classification. It may be particularly advantageous to use markers which permit the identification of a possible collision object, for example, RFID marker. Of course, other sensing devices, in particular, sensors, can also be used to gather further information about a possible collision object in the form of sensing data, as is known in principle. However, the use of sensors and their sensing data already frequently provided on mobile medical units is preferred in any case.

Once again it should be pointed out at this point that an object class can also quite possibly be defined as containing only a single object, for example, if the mobile medical unit is assigned another specific medical device, for example, an imaging device, and is only intended to interact with this or is intended to be able to distinguish between a plurality of assigned medical devices. In this case, the classification for at least the objects of such object classes is to be specifically understood as identification.

An expedient development of at least one embodiment of the invention provides that the control device determines at least one item of feature information describing a feature of the possible collision object from the sensing data and classifies the possible collision object through comparison with the feature for objects of an item of reference information describing at least one object class. If features of the possible collision object can therefore be derived from the sensing data or are in any case even already contained therein, for example, when reading out radio markers, classification can take place through comparison of corresponding feature information with reference information which is available to or at least retrievable by the control device. Examples of features are markers on the possible collision object which may also be optical markers, specifically attached to identify or classify the possible collision object via a camera, and/or features relating to the geometric shape of the possible collision object. Of course, a wide range of other features which can, in particular, also be derived from image data as sensing data of a camera are also conceivable, for example, clearly identifiable components and the like. If radio markers, in particular, RFID markers, are read out, the feature information may also be directly available in the sensing data, for example, as an item of identification information, an item of device class information and the like.

Expediently, the control device can retrieve reference information from a reference information database stored in a storage device of the mobile medical unit and/or an external computing device. Such a reference information database contains the reference information for all the object classes which are to be considered, possibly with the exception of an object class which shows that the possible collision object does not belong to any of the other object classes. The reference information database is preferably stored on an external computing device, in particular, a server, so that a plurality of mobile medical units can retrieve the corresponding reference information, wherein the opportunity furthermore exists to keep this centrally updated. Of course, it is also conceivable to regularly retrieve the reference information database from the external computing device and keep it available locally in the mobile medical unit.

In a particularly advantageous embodiment of the present invention, it is provided that the control device adapts at least one operating parameter with regard to the behavior towards the possible collision object in the context of the autonomous movement operation, in particular, to be used in the calculation and/or the adaptation of the trajectory to be traveled, for possible collision partners of at least one selected object class. As already mentioned, the method according to at least one embodiment of the invention in particular, permits special rules of conduct based on the classification to be specified with respect to objects of at least one selected object class and the automatic operation of movement to thus be configured in a context-sensitive manner which is more flexible and adapted to the situation. For example, it is possible to describe different security requirements, for example, to adhere to a greater distance from people and to select slower speeds than for fixed, static objects. Interactions may also be explicitly permitted.

Static or robust objects may be narrowly circumvented or used for interaction, while personal protection continues to be guaranteed.

A preferred embodiment in this context provides that in a selected object class describing objects intended for interaction with the mobile medical unit, the collision protection function and/or the calculation of the trajectory to be traveled and permitting the intended interaction is adapted. This means the interaction itself can be included in the autonomous operation so that no manual interaction is necessary here. This is achieved without the need for restriction of safety functions for personal protection and damage protection since objects with which interaction is to take place can be recognized by way of classification. For example, when a possible collision object is classified as an object of an object class of objects with which interaction is to take place, a collision course can then be maintained, if applicable with adaptation of the speed so that, for example, docking of patient positioning equipment to a magnetic resonance facility or the approach of a mobile C-arm to patient positioning equipment is enabled.

In particular, contact can be permitted for objects intended for interaction with the mobile medical unit, in particular, for implementation of the interaction and/or with a permissible force of interaction used as an operating parameter. The operating parameter or autonomous operation in general can therefore be specifically adapted to the successful and/or safe performance of the interaction by selecting suitable approach speeds, suitable contact forces and the like.

It is particularly preferred, in the context of at least one embodiment of the present invention, if the at least one object class for which adaptations of the operating parameter are to be made is dynamically selected dependent on a current operating mode and/or a current operational aim. This means that the selected object classes must, at least not fully, be predefined with their consequences, but it is quite possible, depending on the current operating mode or operational aim, to alter behavior with regard to possible collision objects of different object classes. Thus, for example, in the case of mobile patient positioning equipment as a mobile medical unit, initially an operational aim may be to effect X-rays such that docking to an X-ray device is to take place, but later to change the operational aim since a magnetic resonance examination is also to be performed such that the interaction target is then a magnetic resonance facility. With the second operational aim, the X-ray device would then be an obstacle to be circumvented, as is the magnetic resonance facility for the first operational aim. Of course, in this context it is also conceivable that the adaptation takes place as a function of the current operating mode and/or the current operational aim. If, for example, the adapted operating parameters are retrieved from a parameter database, which will be discussed in more detail hereinafter, a plurality of sets of operating parameters can also be stored there which are assigned different operational aims and/or operating modes. In this manner, context sensitivity is extended beyond an improved understanding of the environment to also include the current operating status of the mobile medical unit, thus applying the concept of context-sensitive route planning or trajectory planning more widely.

In an expedient development, provision can be made for the operating parameter to be adapted as a function of at least one object parameter describing an object of the selected object class. The object specified here may be both a general representative object of the selected object class and a specific possible collision object which is classified as a member of the selected object class since it is perfectly possible for object parameters to also be derived from sensing data, which will be examined in more detail hereinafter. The use of object parameters in the method according to the invention permits the behavior of the mobile medical unit to be significantly better adapted to specific properties of the object in general or the possible collision object in particular once again.

It can be provided that at least one dimension of the object of the selected object class and/or a mobility of the object of the selected object class and/or an area of interaction and/or a point of interaction of the object of the selected object class and/or an approach direction to the object of the selected object class and/or a movement parameter, in particular, a direction of movement, of the object of the selected object class are used as object parameters. Of course, further object parameters useful for the autonomous operation of the mobile medical unit are also conceivable.

Specifically, for example, it can be provided that for an object of the selected object class shown as mobile and a current trajectory of autonomous operation to be traveled leading to a collision, a moving away of the possible collision object is awaited, in particular, for a waiting period adapted to the selected object class as an operating parameter. If, based on its object class, the possible collision object is an object which is highly likely to be moving, the decision can be taken for the mobile medical unit to wait until the possible collision object has moved away. In particular, through additional observation on the basis of sensing data, for example, via a camera, in addition, the direction of movement can also be determined and collision-free route planning can be guided hereby. Thus, for example, it can be provided that a circumvention trajectory of autonomous operation described by operating parameters is determined for the possible collision object as a function of the dimensions and/or the direction of movement as an object parameter.

In this manner, the safe, collision-free circumvention of possible collision objects is possible, taking into consideration a current direction of movement of the possible collision object particularly effectively even as it will probably have moved while the mobile medical unit likewise continues to move. Object parameters are furthermore useful if there is provision for an interaction with the possible collision object. Then an interaction trajectory provided for interaction with the possible collision object as a function of the range of interaction and/or the point of interaction and/or the approach direction can be determined as an object parameter. In this manner, for example, a docking point can be precisely determined by the object parameter so that the interaction trajectory can be determined such that approaching takes place from the correct direction at the correct speed and/or a correct force of interaction is specified.

However, in general it can also be said that in the parameterization of rules of conduct according to the properties of a possible collision object, that is to say, the object parameters, operating parameters such as the approach speed, a minimum distance during approach or during circumvention, the waiting time when mobile objects are encountered, the maximum permissible force of interaction when contact is made with objects for which this is permissible, and the like can be adapted. The size and dimensions of possible collision objects provide guidance for adaptation of the radius for evasive maneuvers, depending on the object dimensions of the possible collision object in the direction of travel, and the like. However, it is pointed out that naturally in addition to the object parameters described here and the subsequent adaptation of autonomous operation in general or of operating parameters in particular, naturally operating parameters which are specific to an object class or adapted to the object class can also be taken into consideration, for example, minimum distances and/or dynamic limits.

Preferably, at least some of the object parameters can be determined by evaluating the sensing data with regard to the possible collision object. In this manner, the sensing data will expediently be given a further intended purpose to further improve the context-sensitive operation for movement of the mobile medical unit. If feature information is determined, the results obtained can also continue to be used particularly advantageously for determination or as object parameters; additional properties of the possible collision object can be determined from the sensing data by way of image processing or similar data evaluation algorithms for sensor data and/or in sensing data retrieved from radio markers.

In an advantageous development of at least one embodiment of the present invention, it is provided that at least some of the operating parameters to be used relating to a selected object class and/or at least some of the object parameters relating to an object representative of the selected object class are retrieved from a parameter database stored in a or the storage device of the mobile medical unit and/or an or the external computing device, which in particular corresponds to the reference information database. This means that provision can also be made for the operating parameters and/or the object parameters to be kept available in a database, here a parameter database which may be local and/or external. In this case too, a parameter database which is at least partially external, that is to say, for example, available on a server, which can be accessed by way of a communication link, is preferred as the data therein can then be used for a plurality of mobile medical units. It is particularly advantageous if a comparison takes place with reference information if the parameter database and the reference information database are consolidated as an overall database in which object classes are assigned both the reference information as well as operating parameters and/or object parameters.

As already indicated, a minimum distance and/or an approach speed and/or an approach speed profile and/or a maximum permissible force of interaction can be expediently used as operating parameters, wherein naturally a multiplicity of other operating parameters which, in particular, are used for the planning of a trajectory to be traveled are conceivable and can be taken into consideration.

In general, in the context of at least one embodiment of the present invention, it is preferred that for a possible collision object assigned to an object class comprising a person, compared to a normal operating mode a reduced dynamic is activated in the safety operating mode permitting autonomous operation. In this connection, it is pointed out that the activation of another operating mode is naturally accompanied by an adaptation of operating parameters and thus the embodiments relating to the operating parameters can also be applied analogously with regard to operating modes. In this manner, particular protection of persons who may find themselves in the vicinity of the mobile medical unit can be ensured in that object classes containing persons may not only be assigned greater safety distances, but overall endeavors are also made to achieve a slower, more cautious operation of the mobile medical unit.

It is particularly advantageous if a plurality of object classes comprising persons are used, in particular, an object class for personnel and/or an object class for patients and/or an object class for visitors and/or an object class for children, wherein different safety operating modes are used for different experiences when dealing with persons with mobile medical units. In particular, the safety may increase, the less experience can be attributed to the corresponding group of people with regard to mobile medical units. While, for example, personnel are familiar with mobile medical units from their daily work and are excellently equipped to deal with these, patients have less of this familiarization and experience, but nevertheless to a greater extent.

In contrast, visitors, in particular children, may have extremely limited experience of mobile medical units, so that the greatest possible safety can be provided by a safety operating mode assigned to these groups of people. Thus, for example, with regard to children, besides a greater predetermined safety distance when circumventing children, a slower speed is possible in order to be less frightening for children and to minimize the risk of injury, in particular, when children are playing.

A further particularly preferred embodiment of the invention provides that the current position of the mobile medical unit within an operating environment is determined via a position determination device, according to which the property information assigned to the current position is retrieved from a map database and taken into consideration in the autonomous operation of the mobile medical unit. In this case, possibilities for determining the position, as can also be used in the method according to at least one embodiment of the invention, are known in principle and are also used, for example, for basic navigation in extended navigation environments, for example, hospitals and/or radiology departments. Various possibilities for determining the position by way of radio, cameras, markers and the like can be used in the context of the present invention.

Since the mobile medical unit can be located within its navigation environment, however, a plurality of further items of information can be provided in a map database, in particular, locally in the aforementioned storage device of the mobile medical unit and/or in the external computing device, which can be taken into consideration in the autonomous operation of the mobile medical unit, in particular, in the planning of a trajectory to be traveled. The property information may comprise static properties relevant to behavior towards other objects and/or in particular, current status information dynamically updated in the map database.

Specific static properties may, for example, relate to traction and/or the bypass space available, while an opening status of a door and/or information describing a current construction site and/or problem area can be used as dynamic status information. In this way, for example, critical points for evasive maneuvers due to a particularly narrow corridor and the like can be identified and dynamic properties of the current environment can also be considered particularly advantageously, for example, self-closing doors, temporary changes of the navigation area available as a result of structural and/or technical measures (=construction site), changes in the navigation conditions, for example, changes in traction as a result of current changes in the condition of the soil, for example, moisture, and the like. In this way, the context sensitivity of the autonomous operation of the mobile medical unit is also extended to general environmental properties not related to special possible collision objects, in particular, also current events for which the map database is particularly advantageously filed on an external computing device and is constantly updated there.

In general, as is also apparent from the examples discussed, a plurality of different object classes can be employed in the context of the present invention so that at least one person class and/or at least one diagnostic device class and/or at least one patient transport device class and/or at least one therapy device class can be used as object classes.

In addition to the method, at least one embodiment of the invention also relates to a mobile medical unit, which has at least one sensing device for detecting possible collision objects in the environment of the unit and a control device which evaluates the sensing data of the sensing device and which is designed to at least partially autonomously operate the movement of the unit while performing the collision protection function which is characterized in that the control device is designed to perform the method according to at least one embodiment of the invention.

All the embodiments relating to the method according to the invention can be applied analogously to the mobile medical unit according to the embodiments of the invention so that the aforementioned advantages can also be retained with this. In particular, the control device may therefore have a trajectory detection unit for a trajectory to be traveled and a classification unit, wherein the classification unit evaluates the sensing data and as a consequence directly or indirectly adapts operating parameters to determine the trajectory to be traveled. The mobile medical unit may also have a storage device and/or a communication device for communication with an external computing device, wherein a reference information database and/or a parameter database and/or a map database, preferably an overall database combining all these databases, can be stored on the storage device and/or the external computing device.

Overall, it should be noted with regard to embodiments of the present invention, that the mobile medical unit is naturally intended for autonomous movement, in particular inside buildings, for example, in doctors' offices and/or radiology departments and/or hospitals, as the navigation environment. The mobile medical unit can preferably be patient positioning equipment and/or a patient transport device and/or a component of a medical imaging device and/or a mobile medical robot.

FIG. 1 shows a schematic diagram of an example embodiment of a mobile medical unit 1 involving, in particular, mobile patient positioning equipment and/or a patient transport device, for example, a mobile patient table which is designed for at least partially autonomous operation of movement.

The mobile medical unit 1 has a control device 2 for this purpose which is designed to determine a trajectory to be traveled and to appropriately activate drive device(s) 3 and steering device(s) 4 for wheels 5 of the unit 1. To detect the environment in which the mobile medical unit 1 is moved, it also has sensing devices 6, wherein in the present case a camera 7 is shown as an imaging sensor and an RFID readout device 8 for a radio marker 10 on a potential collision object here only touched upon, here an RFID chip. In addition, possible collision objects 9 may also have optical markers 11 which are recognizable as sensing data by way of image processing of the image data recorded with the camera 7. For navigation in the navigation environment, in the present case, the interior of a building, for example of a hospital or a doctor's office, the control device 2 further employs data of a position determination device 12.

The present mobile medical unit 1 designed as patient positioning equipment and/or a patient transport device can dock to various medical imaging devices, in the present example a magnetic resonance facility for which it accordingly further comprises docking device(s) 18 which interact with a corresponding docking device.

To enable context-sensitive autonomous movement operation, in particular, in route planning, that is to say, the determination of the trajectory to be traveled, to generally observe other objects not only in the context of a collision protection function but to be able to take into consideration their special properties and the properties of the environment as it currently exists, the control device 2 also has access by way of a communication device 13 or in a storage device 14 to an overall database 15 which is shown in the present case as stored on an external computing device 16, to which a wireless communication link 17 can be established by way of the communication device 13.

In addition to a map database, the overall database comprises the property information for static and dynamic properties of the currently used environment, also a combined parameter and reference information database in which a certain number of object classes are assigned reference information which can compare the control device 2 for assigning a detected possible collision object 9 to an object class with feature information derived from the sensing data of the sensing devices 6. Furthermore, the combined parameter and reference information database contains at least one set of values for objects of the object class of the operating parameters to be used and properties of a representative object of object parameters describing the object class, from which operating parameters can be derived, if applicable.

Figure 2:
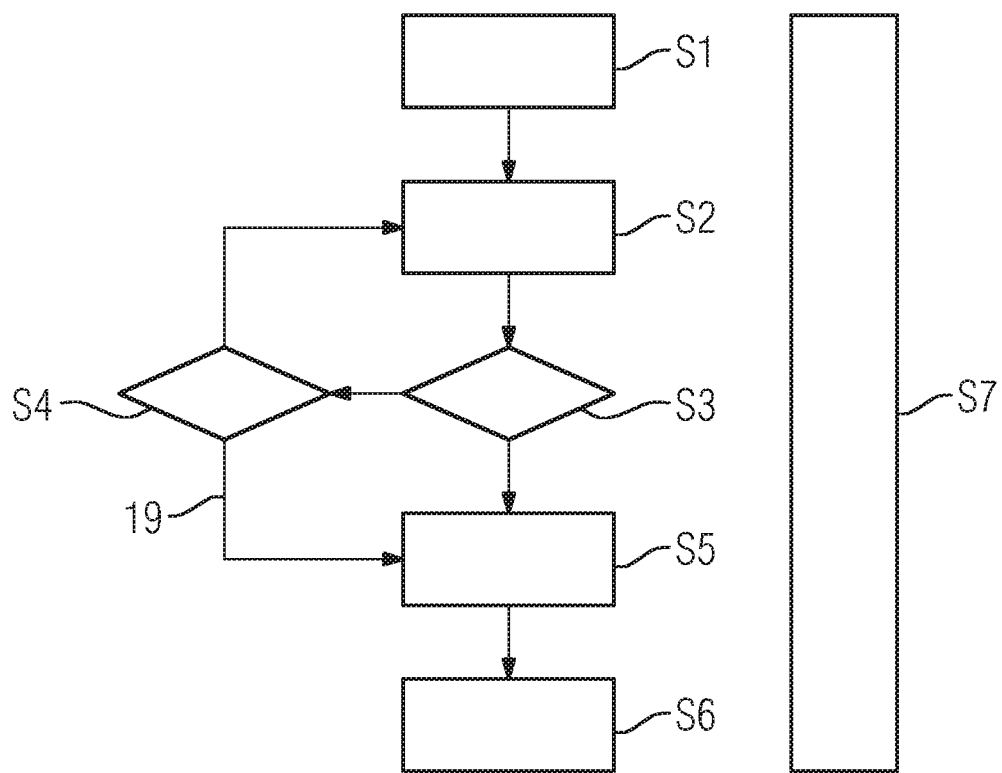
FIG. 2 A flow chart of an example embodiment of the method according to the invention, FIG. 3 A first navigation situation, and FIG. 4 A second navigation situation.

The control device 2 is designed to perform an example embodiment of the method according to an embodiment of the invention, as is to be explained in more detail with the aid of the flow chart in FIG. 2. FIG. 2 shows the procedure when a possible collision object 9 is determined by the sensing devices 6 in the prospective path of movement of the mobile medical unit 1, that is to say, along the trajectory to be traveled.

For this purpose, in a step S1 first the sensing data is used to determine feature information which describes at least one feature of the possible collision object 9. Feature information can be derived, for example, by way of image processing from geometric shapes derived from image data of the camera 7 and other feature information describing visually striking features, for example, markers 11, as well as by reading out the feature information obtained from the radio marker 10, for example, identification information, device class information and the like. When determining feature information from image data or general sensor data and other sensing data, object parameters to be taken into consideration later, for example, relating to the dimensions and/or size, can also be deduced already.

In a step S2, the feature information is compared to corresponding reference information retrieved from the overall database 15 for an object class to be examined. If, cf. step S3, there is no consensus, in a step S4 it is possible to examine whether there are any further object classes in which a comparison should take place, then branching back to step S2 again. However, if it is established in step S4 that the possible collision object 9 is apparently not assigned to the object classes specifically detected in the overall database due to the failed comparisons, the possible collision object is assigned to an object class of remaining objects in accordance with the arrow 19; however, if in comparison it has already been found previously, cf. step S3, that there is a sufficient correlation with reference information of a particular reference class, in step S5 the possible collision object 9 is assigned to this object class. Since object classes may also only contain one object, identification is therefore also possible as a special form of classification.

Since the possible collision object 9 was classified in step S5, in a step S6 the autonomous movement operation is adapted on the basis of the object class determined for the possible collision object 9. During this adaptation, a current operating mode or a current operational aim of the mobile medical unit 1 is also taken into consideration, for example, that docking is to take place by way of the docking device(s) to a magnetic resonance facility, which represents an object of an individual object class of magnetic resonance facilities.

Firstly, the operating parameters and object parameters assigned to the object class of the possible collision object 9 are retrieved from the overall database 15. If there are a plurality of sets of values for operating parameters, these usually comprise a standard set and an interaction set. If the current operating mode or the current operational aim indicates that interaction with objects of this object class is desired, the interaction set of operating parameters is selected and set. Otherwise, the standard set will be used. Operating parameters may comprise, for example, a minimum distance, an approach speed, an approach speed profile, a maximum permissible force of interaction and the like. They are therefore specifically taken into consideration when determining the trajectory of the mobile medical unit 1 to be traveled, which also applies to the properties of the possible collision object 9 of the object parameters describing the object class which may be, for example, a dimension, a mobility, a range of interaction, a point of interaction, an approach direction, or a movement parameter, in particular a direction of movement. In this case, it should be pointed out again that the object parameters are, in particular, also at least partially determined from the sensing data. The properties specifically described by the object parameters of the possible collision object are therefore also taken into consideration in determining the trajectory to be traveled and therefore also result in certain operating parameters adapted for the presence of the possible collision object 9 of the object class.

It should be noted that the method according to FIG. 2 is naturally always performed when a new possible collision object is detected. Naturally, a plurality of classified possible collision objects 9 may also find their way into the autonomous movement operation.

A plurality of possibilities exists for the effect of the adapted operating parameters on the autonomous movement operation of the mobile medical unit 1. For example, in the case of an object displayed as a movable object of the object class of the possible collision object 9 and a current trajectory to be traveled leading to a collision, a displacement of the possible collision object 9 can be awaited. A more advantageous operating parameter here may comprise a waiting period for the special object class which shows the probability of a movement of the possible collision object 9. In a further example, the previously traveled trajectory can be changed to determine a circumvention trajectory for the possible collision object 9 and to therefore circumvent this, wherein besides operating parameters such as the minimum permitted distance and permitted movement speeds, the dimensions and the direction of movement can be taken into consideration as object parameters. A special case exists when a possible collision object 9 provided for interaction has been established on the basis of classification, for then an interaction trajectory can be determined accordingly as a function of parameters such as the range of interaction, the point of interaction, the approach direction, the approach speed or the approach speed profile, the maximum permitted acting force and the like, in other words, the interaction, in the example described here the docking, can be included in the autonomous operation.

An important operating parameter with regard to object classes can also be a maximum permissible speed of movement in a predefined specification range around possible collision objects of an object class, in particular for person classes. A plurality of person classes or object classes comprising people are preferably used in the process, in the present case, an object class for personnel, an object class for patients, an object class for visitors and an object class for children, wherein the maximum permissible speed of movement for children, who have the least experience with mobile medical units 1, is the lowest and can increase with increasing experience in dealing with mobile medical units 1 so that overall the maximum permitted speed of movement for personnel is greater than for patients, which in turn is greater than for visitors, which in turn is greater than for children.

It should be noted at this point that during the autonomous movement operation, as indicated by step S7 in FIG. 2, the map database is also constantly used as part of the overall database 15. Since the position of the unit 1 in the navigation environment assigned to it is known thanks to the position determination device 12, static properties and dynamic properties of the environment at the current position can be taken into consideration, for example, whether a door ahead is just closing, whether there is a construction site or a bottleneck which is not critical for evasive maneuvers, and the like.

FIGS. 3 and 4 show example navigation situations in which the mobile medical unit 1 can find itself.

FIG. 3 shows a case in which the mobile medical unit 1 encounters two possible collision objects 9 along its planned trajectory to be traveled 20, namely a person 21 and an X-ray device 22. If the person 21 is detected and classified as a person (if applicable, more precisely, as personnel), the mobile medical unit 1 first switches to a safety operating mode in which the maximum permitted speed of movement is reduced. It will stop at a position 23 at a predetermined distance in front of the person 21 and wait for a waiting period to see whether the person 21 does not move away after the latter is displayed as movable. If the person 21 has moved away, the original spatial course of the trajectory 20 can be continued again. Otherwise, a circumvention trajectory 24 is calculated and used while observing a minimum distance from the person 21.

Since the mobile medical unit 1 is to dock to a magnetic resonance facility, it will establish that the X-ray device 22 is not such a magnetic resonance facility in that the X-ray device 22 is accordingly classified as belonging to an X-ray device class. Since the X-ray device 22 does not usually move either, a circumvention trajectory 25 is immediately determined and used here which may be able to pass the X-ray device 22 more closely, the dimensions/size of which are also known by the object parameters.

In FIG. 4, in a further navigation situation, the mobile medical unit 1 has arrived in a space 26 which contains a magnetic resonance facility 27 as a possible collision object 9 along the currently planned trajectory to be traveled 20. Since the mobile medical unit 1 is to connect to a magnetic resonance facility 27 by way of its docking device(s) 18, in that a local docking device 28 is used, after classification of the magnetic resonance facility 27 as belonging to a magnetic resonance facility class, the collision is not avoided since an interaction is actually desired.

In other words, a collision protection function is not used in this case. Instead the adapted operating parameters can be used, wherein here the interaction set, and the object parameters which describe the point of interaction and the approach direction are used to determine an optimally suitable interaction trajectory 29, wherein it follows from the operating parameters of the interaction set that a certain approach speed should be given and a certain force of interaction should not be exceeded. In this manner, automatic docking is also possible in the autonomous movement operation of the mobile medical unit 1, in particular, without a collision protection function preventing this.

It should be noted that other mobile medical units 1 are also conceivable, for example, autonomously movable components of imaging devices, in particular, mobile C-arms and the like.

Although the invention was illustrated and described in more detail by the preferred example embodiment, the invention is not limited by the disclosed examples and other variations can be derived from this by a person skilled in the art without departing from the scope of protection of the invention.

LIST OF REFERENCE CHARACTERS

1 Mobile medical unit
2 Control device
3 Drive device(s)
4 Steering device(s)
5 Wheel
6 Sensing device
7 Camera
8 RFID readout device
9 Collision object
10 Radio marker
11 Optical marker
12 Position determination device
13 Communication device
14 Storage device
15 Overall database
16 Computing device
17 Communication link
18 Docking device(s)
19 Arrow
20 Trajectory
21 Person
22 Person
23 Position
24 Circumvention trajectory
25 Circumvention trajectory
26 Area
27 Magnetic resonance facility
28 Docking device
S1-S6 step

The invention claimed is:

1. A method for operating an at least partially autonomously moving, mobile medical unit including at least one sensing device to detect possible collision objects in an environment of the unit and including a control device, to evaluate sensing data of the at least one sensing device and designed to at least partially autonomously operate movement of the mobile medical unit while performing a collision protection function, the method comprising:
classifying a possible collision object, described by the sensing data, by evaluating the sensing data and taking, into consideration in the autonomous operation of the unit, the possible collision object classified by the classifying;
adapting, via the control device, at least one operating parameter relating to a behavior towards the possible collision object classified, in a context of at least partially autonomous movement operation of the mobile medical unit, for possible collision partners of at least one selected object class, wherein at least one of at least one person class, at least one diagnostic device class, at least one patient transport device class, and at least one therapy device class are used as object classes.

2. The method of claim 1, wherein the at least one sensing device comprises at least one imaging sensor, and wherein the control device is configured to evaluate the sensing data of at least one of the at least one imaging sensor by image processing.

3. The method of claim 2, wherein the control device is configured to retrieve the reference information from a reference information database stored in at least one of a storage device of the mobile medical unit and an external computing device.

4. The method of claim 2, wherein the at least one imaging sensor is a camera.

5. The method of claim 1, wherein the control device is configured to determine at least one item of feature information describing a feature of the possible collision object from the sensing data and is configured to classify the possible collision object by comparison with reference information describing the feature for objects of at least one object class.

6. The method of claim 5, wherein a marker on at least one of the possible collision object and a feature concerning a geometric shape of the possible collision object is used as the feature.

7. The method of claim 5, wherein the control device is configured to retrieve the reference information from a reference information database stored in at least one of a storage device of the mobile medical unit and an external computing device.

8. The method of claim 1, wherein in a selected object class describing intended objects intended for interaction with the mobile medical unit, at least one of a collision protection function and calculation of the trajectory to be traveled is adapted to an intended interaction in a permitted manner.

9. The method of claim 8, wherein for objects intended for interaction with the mobile medical unit, a contact at least one of for performance of the interaction and with a permissible force of interaction used as an operating parameter, is permitted.

10. The method of claim 1, wherein at least one of
at least one object class, for which the adapting of the at least one operating parameter is to be undertaken, is dynamically selected depending on at least one of a current operating mode and a current operational aim; and
the adapting of the at least one operating parameter takes place as a function of at least one of the current operating mode and the current operational aim.

11. The method of claim 1, wherein the adapting of the at least one operating parameter occurs as a function of at least one object parameter describing an object of the selected object class.

12. The method of claim 11, wherein the object parameters include at least one of at least one of
an extension of the object of the selected object class, a mobility of the object of the selected object class, a range of interaction, a point of interaction of the object of the selected object class, an approach direction to the object of the selected object class, a movement parameter including a direction of movement of the object of the selected object class.

13. The method of claim 12, wherein for an object displayed as movable of the selected object class and a current trajectory to be traveled resulting in a collision of the autonomous operation, at least one of a moving away of the possible collision object is awaited for a waiting period adapted to the selected object class as an operating parameter,
at least one of a circumvention trajectory described by operating parameters of the autonomous operation for the possible collision object as a function of the dimensions and direction of movement as object parameters is determined, and
an interaction trajectory intended for interaction with the possible collision object is determined as an object parameter as a function of at least one of the range of interaction, the point of interaction and the approach direction.

14. The method of claim 11, wherein at least some of the object parameters are determined by evaluating the sensing data relating to the possible collision object.

15. The method of claim 1, wherein the at least one operating parameter includes a plurality of operating parameters and wherein
at least some of the plurality of operating parameter, to be used relating to a selected object class, and at least some of the plurality of object parameter relating to an object representative of the selected object class, are retrieved from a parameter database stored in at least one of a storage device of the mobile medical unit and an external computing device.

16. The method of claim 1, the at least one operating parameter includes a plurality of operating parameters and wherein at least one of a minimum distance, an approach speed, an approach speed profile, and a maximum permissible force of interaction are used as the plurality of operating parameters.

17. The method of claim 1, wherein in a possible collision object assigned to an object class comprising a person, a safety operating mode permitting a reduced dynamic during autonomous operation relative to a normal operating mode is activated.

18. The method of claim 17, wherein a plurality of object classes comprising people are used and wherein different safety operating modes for different experiences in dealing with people with mobile medical units are used.

19. The method of claim 18, wherein the plurality of object classes comprising people include an object class for personnel, an object class for patients, an object class for visitors, and an object class for children.

20. The method of claim 1, wherein the current position of the mobile medical unit within an operating environment is determined via a position determination device, according to which property information assigned to the current position is retrieved from a map database and taken into consideration during the autonomous operation of the mobile medical unit.

21. The method of claim 20, wherein the property information comprises at least one of static properties relevant to behavior towards other objects and current status information dynamically updated in the map database.

22. The method of claim 21, wherein the static properties, used as status information, relate to at least one of traction, the available bypass space, information describing an opening status of a door, a current construction site and problem area.

23. The method of claim 1, wherein the at least one sensing device comprises a readout device for a radio marker of the possible collision object.

24. The method of claim 23, wherein the readout device is an RFID chip.

25. A mobile medical unit, comprising:
at least one sensing device to detect possible collision objects in an environment of the mobile medical unit; and
a control device to evaluate sensing data of the at least one sensing device and designed to at least partially autonomously operate movement of the mobile medical unit while performing a collision protection function, the control device being further configured to
classify a possible collision object, described by the sensing data, by evaluating the sensing data and taking, into consideration in the autonomous operation of the unit, the possible collision object classified by the classifying; and
adapt at least one operating parameter relating to a behavior towards the possible collision object classified, in a context of at least partially autonomous movement operation of the mobile medical unit, for possible collision partners of at least one selected object class, wherein at least one of at least one person class, at least one diagnostic device class, at least one patient transport device class, and at least one therapy device class are used as object classes.

26. The mobile medical unit of claim 25, wherein the at least one sensing device comprises at least one imaging sensor, and wherein the control device is configured to evaluate the sensing data of at least one of the at least one imaging sensor by image processing.

27. The mobile medical unit of claim 25, wherein the control device is configured to determine at least one item of feature information describing a feature of the possible collision object from the sensing data and is configured to classify the possible collision object by comparison with reference information describing the feature for objects of at least one object class.

28. The mobile medical unit of claim 27, wherein the control device is configured to retrieve the reference information from a reference information database stored in at least one of a storage device of the mobile medical unit and an external computing device.

* * * * *